United States Patent [19]

Jackson et al.

[11] Patent Number: 5,395,853

[45] Date of Patent: Mar. 7, 1995

[54] ANTI-ATHEROSCLEROTIC DIARYL COMPOUNDS

[75] Inventors: William P. Jackson; Clifford J. Harris; Richard J. Arrowsmith; John G. Dann; Kevin J. O'Connor; Robert F. G. Booth, all of Beckenham, United Kingdom

[73] Assignee: Burroughs Wellcome Co., Research Triangle Park, N.C.

[21] Appl. No.: 157,685

[22] Filed: Nov. 24, 1993

Related U.S. Application Data

[62] Division of Ser. No. 971,252, Nov. 5, 1992, Pat. No. 5,290,814, and Ser. No. 439,552, Nov. 20, 1989, abandoned.

[30] Foreign Application Priority Data

Nov. 21, 1988 [GB] United Kingdom ............... 8827152

[51] Int. Cl.⁶ .................. C07C 275/28; C07C 279/18; A61K 31/17; A61K 31/155

[52] U.S. Cl. ..................... 514/596; 514/506; 514/523; 514/529; 514/584; 514/585; 514/599; 514/617; 514/634; 514/646; 514/648; 514/649; 514/654; 558/390; 558/391; 558/395; 560/38; 560/49; 560/72; 560/73; 564/26; 564/48; 564/74; 564/182; 564/184; 564/237; 564/238; 564/305; 564/323; 564/336; 564/374; 564/441

[58] Field of Search ................... 564/54; 514/596, 824

[56] References Cited

U.S. PATENT DOCUMENTS

| 4,269,829 | 5/1981 | Seidel et al. | 424/211 |
|---|---|---|---|
| 4,387,106 | 6/1983 | De Vries et al. | 424/322 |
| 4,564,630 | 1/1986 | Toth et al. | 514/478 |
| 4,603,145 | 7/1986 | De Vries et al. | 514/539 |
| 4,716,175 | 12/1987 | Hoefle et al. | 514/357 |
| 4,824,843 | 4/1989 | Hoefle et al. | 514/228.8 |
| 5,015,644 | 5/1991 | Roth et al. | 514/247 |

FOREIGN PATENT DOCUMENTS

| 0017484A1 | 10/1980 | European Pat. Off. |
| 041145B1 | 12/1984 | European Pat. Off. |
| 0242610A1 | 10/1987 | European Pat. Off. |
| 0252524A2 | 1/1988 | European Pat. Off. |
| 0283742A3 | 9/1988 | European Pat. Off. |
| 0297610A1 | 1/1989 | European Pat. Off. |
| 0335374 | 10/1989 | European Pat. Off. |
| 0335375 | 10/1989 | European Pat. Off. |
| 0344425 | 12/1989 | European Pat. Off. |
| 0370740A1 | 5/1990 | European Pat. Off. |
| 0450660A1 | 10/1991 | European Pat. Off. |
| 2340874 | 2/1974 | Germany . |
| WO84/02704 | 7/1984 | WIPO . |

OTHER PUBLICATIONS

R. R. Schmidt, et al., Chem., Ber., 105, 1634–1645 (1972), Synthese von Heterocyclen durch Thermolyse von 0-substituierten aromatischen Diazonium–Ione.

Alberola et al. Chem. Abst 97:38593m (1982).

Elkobaise et al. II Chem. Abst. 54:14175 (1960).

Elkobaise et al I Chem. Abst. 52:18312 (1958).

W. D. Zahler, et al., Intramolekulare Arylierungen in der Diphenylmethan–Reihe, pp. 765–770, 1963.

Chem. Abstract–p. 585, vol. 98, 1983, 215869.

Chem Abstract–p. 795, vol. 83, 1975, 9609, with Collective Index.

Chem. Abstract–p. 539, vol. 97, 1982.

H. Horino, et al. J. Org. Chem., 1981; vol. 46, pp. 4416–4422, Ortho Vinylation of Aromatic Amides via Cyclopalladation Complexes.

K. Pelz; et al., Collection Cxechoslov. Chem. Commun., vol. 33, (1968), Neurotrpe und Psychotrope Substanzen XXIV. 2-Substituierte 1,2-Diphenylathan Derivate Versuche Einer Neuen Synthese Der Dibenz/b, flazocin–Derivate.

W. J. van der Burg, et al., Jan., 1970, vol. 13; pp. 35–39; Antiserotonin Piperazines, A Novel Type of Substituted Peperazine with High Anti-serotonin Potency[1].

P. DeMayo, et al., J.C.S. Chem. Comm., 1979, pp. 499–500 Synthesis: Quinolines.

Primary Examiner—Peter O'Sullivan
Attorney, Agent, or Firm—Donald Brown; Lawrence A. Nielsen

[57] ABSTRACT

The present invention is concerned with compounds of formula (I)

(Abstract continued on next page.)

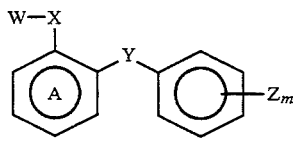

(I)

wherein
m is 0 or 1;
W is hydrogen, a $C_{1-16}$ straight, branched, or cyclic alkyl group, or a $C_{2-16}$ straight, branched, or cyclic alkenyl or alkynyl group, or Ph(CH$_2$)$_n$— where Ph is phenyl and n is an integer of from 0 to 2, the phenyl group being optionally substituted by one or more atoms or groups independently selected from halogen, hydroxy, nitro, $C_{1-4}$ alkoxy and $C_{1-4}$ alkyl wherein one or more of the hydrogen atoms in said alkyl group is optionally replaced by halogen, or R$^1$NHCO— where R$^1$ is hydrogen or a $C_{1-6}$ alkyl group, or R$^2$CONH— where R$^2$ is hydrogen or a $C_{1-6}$ alkyl group;

X is —(CH$_2$)$_p$NHCONH, where p is an integer of from 0 to 2,
|

-continued

—NHCONHCH$_2$, —CONH, —NHCOCH$_2$, —NHCOO,
| | | |

—CSNH, —NHCSNH, —NHC(:NH)NH, —NHC(:NCN)NH,
| | | |

—NHC(:CHCN)NH, —NHC(:CHNO$_2$)NH, or
| |

—CH(A)CONH where A is halogen;
|

Y is —(CH$_2$)$_q$, where q is an integer of from 1 to 3, or —CH=CH— (E or Z);

Z is a $C_{1-6}$ alkyl group optionally substituted by one or more independently selected polar groups; and ring A is optionally substituted by one or more atoms or groups independently selected from halogen, hydroxy, nitro, $C_{1-4}$ alkoxy and $C_{1-4}$ alkyl wherein one or more of the hydrogen atoms in said alkyl group is optionally replaced by halogen;

provided said compound of formula (I) is not N-{2-[(4-methyl-phenyl)methyl]phenyl}acetamide or α-(p-tolyl)-o-cresol carbanilate; and salts, solvates and physiologically functional derivatives thereof, processes for the preparation of these compounds, pharmaceutical formulations containing them and their use in medicine.

2 Claims, No Drawings

ANTI-ATHEROSCLEROTIC DIARYL COMPOUNDS

This is a continuation divisional of application(s) U.S. No. 07/971,252, filed on Nov. 5, 1992, now U.S. Pat. No. 5,290.814, and 7/439552 filed Nov. 20, 1989, now abandoned.

The present invention is concerned with new diaryl compounds, processes for their preparation, compositions containing them and their use in medicine, particularly in the prophylaxis or treatment of atherosclerosis.

Intracellular cholesterol ester metabolism in the arterial wall is handled by a variety of enzymes including acyl coenzyme A: cholesterol acyl transferase (ACAT), cholesteryl ester hydrolase (CEH), acid cholesterol hydrolase and cholesteral esterase. Of these, ACAT and cholesteryl ester hydrolase appear to control the steady state concentration of cholesterol ester in the arterial wall:

ACAT may also play a key role in the gastrointestinal absorption of cholesterol on the basis that: (a) more than 90% of the cholesterol which appears in the lymph is esterified, (b) substantial ACAT activity has been observed in the intestinal mucosal cells of several animal species, (c) the site of greatest intestinal ACAT activity is the jejunum where the majority of cholesterol absorption occurs, (d) ACAT activity in the jejunum parallels increases in dietary cholesterol, and (e) ACAT activity is significantly enhanced in animals having experimental atherosclerosis and in atherosclerotic human tissue and cell cultures.

We have now discovered a novel class of diaryl compounds which exhibit ACAT inhibitory activity and which are particularly useful as hypolipidaemics as well as for decreasing the steady state concentration of cholesterol and cholesterol ester in the arterial wall and thereby retarding the build-up of atherosclerotic lesions.

According to the present invention, therefore, there are provided compounds of formula (I)

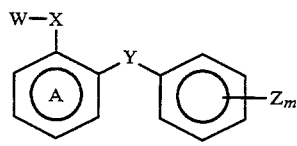

wherein
m is 0 or 1;
W is hydrogen, a $C_{1-16}$ straight, branched, or cyclic alkyl group, or a $C_{2-16}$ straight, branched, or cyclic alkenyl or alkynyl group, or
Ph(CH$_2$)$_n$— where Ph is phenyl and n is an integer of from 0 to 2, the phenyl group being optionally substituted by one or more atoms or groups independently selected from halogen, hydroxy, nitro, $C_{1-4}$ alkoxy and $C_{1-4}$ alkyl wherein one or more of the hydrogen atoms in said alkyl group is optionally replaced by halogen, or
$R^1$NHCO— where $R^1$ is hydrogen or a $C_{1-6}$ alkyl group, or $R^2$CONH— where $R^2$ is hydrogen or a $C_{1-6}$ alkyl group;

X is —(CH$_2$)$_p$NHCONH, where p is an integer of from 0 to 2,

—NHCONHCH$_2$, —CONH, —NHCOCH$_2$, —NHCOO,

—CSNH, —NHCSNH, —NHC(:NH)NH, —NHC(:NCN)NH,

—NHC(:CHCN)NH, —NHC(:CHNO$_2$)NH, or

—CH(A)CONH where A is halogen;

Y is —(CH$_2$)$_q$—, where q is an integer of from 1 to 3, or —CH=CH— (E or Z);
Z is a $C_{1-6}$ alkyl group; and
ring A is optionally substituted by one or more atoms or groups independently selected from halogen, hydroxy, nitro, $C_{1-4}$ alkoxy and $C_{1-4}$ alkyl wherein one or more of the hydrogen atoms in said alkyl group is optionally replaced by halogen;
provided said compound of formula (I) is not N-{2-[(4-methyl-phenyl)methyl]phenyl}acetamide or α-(p-tolyl)-o-cresol carbanilate; and salts, solvates and physiologically functional derivatives thereof.

The term "cyclic group" as used herein includes groups wherein the cyclic moiety is located at the end of or along the length of a straight or branched alkyl, alkenyl, or alkynyl group, for example, —CH$_2$CH(C$_6$H$_{11}$)CH$_3$.

The compounds of the proviso are already known per se, viz. N-(2-[(4-methylphenyl)methyl]phenyl)acetamide Chem. Ber. 105, 1634 (1972) α-(p-tolyl)-o-cresol carbanilate Chem. Bet. 96, 765 (1963) but there is no disclosure or suggestion in these references that the compounds in question may be used in therapy.

Salts of compounds of formula (I) suitable for use in medicine are those which are physiologically acceptable. However, non-physiologically acceptable salts are within the scope of the present invention for use as intermediates in the preparation of the compounds of the invention and their physiologically acceptable salts, solvates and physiologically functional derivatives.

The "physiologically functional derivatives" referred to herein are compounds which are converted in vivo to a compound of formula (I) or to one of its physiologically acceptable salts or solvates.

Preferred compounds of formula (I) having particularly good ACAT inhibiting properties include those wherein
W is hydrogen, $C_{7-11}$ straight alkyl, cyclohexyl, cyclohexylmethyl, or 1,1-dimethylprop-2-ynyl, or phenyl or benzyl, or
n-C$_4$H$_9$NHCO—, or
n-C$_3$H$_7$CONH—;

X is —(CH$_2$)$_p$NHCONH, where p is an integer of from 0 to 2,

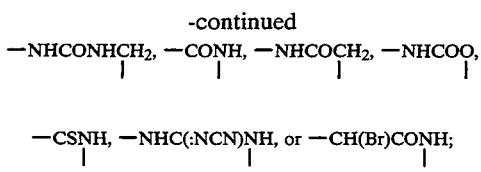

Z is hydrogen (i.e. m is 0) or, when m is 1, p-isobutyl or p-neopentyl; and ring A is unsubstituted or disubstituted at the 2,4- or 3,5-positions by fluorine atoms;

and physiologically acceptable salts, solvates and physiologically functional derivatives thereof. Particularly preferred compounds of formula (I) having exceptionally desirable ACAT inhibiting properties include those wherein W is n-heptyl;

X is —NHCONH, —NHCOCH₂, or —NHCOO;

Y is —(CH₂)₂—;

m is 1 and Z is p-isobutyl or p-neopentyl; and ring A is disubstituted at the 2,4-positions by fluorine atoms;

and physiologically acceptable salts, solvates and physiologically functional derivatives thereof.

The most preferred compound of formula (I) is N-heptyl-N'-(2,4-difluoro-6-{2-[4-(2,2-dimethylpropyl)-phenyl]ethyl}phenyl urea and its physiologically acceptable salts, solvates and physiologically functional derivatives.

According to further aspects of the invention, there are also provided:

(a) compounds of formula (I) and pharmaceutically acceptable salts, solvates and physiologically functional derivatives thereof for use in therapy;

(b) pharmaceutical formulations comprising a compound of formula (I) and/or one of its pharmaceutically acceptable salts, solvates, or physiologically functional derivatives and at least one pharmaceutical carrier or excipient;

(c) the use of a compound of formula (I) or of a pharmaceutically acceptable salt, solvate, or physiologically functional derivative thereof in the manufacture of a medicament for the prophylaxis or treatment of a clinical condition for which an ACAT inhibitor is indicated;

(d) a method for the prophylaxis or treatment of a clinical condition in a mammal, such as a human, for which an ACAT inhibitor is indicated which comprises the administration of a therapeutically effective amount of a compound of the formula (I) or of a pharmaceutically acceptable salt, solvate, or physiologically functional derivative thereof to said mammal; and (e) processes for the preparation of compounds of formula (I) (including salts, solvates and physiologically functional derivatives thereof).

With regard to aspects (a), (c) and (d), the ability of compounds of the formula (I) to inhibit ACAT activity renders them useful as hypolipidaemics and in reducing the steady state concentration of cholesterol and cholesterol ester in the arterial wall, thereby retarding the build-up of atherosclerotic lesions and providing application for these compounds in the prophylaxis or treatment of atherosclerosis.

Hereinafter all references to "compound(s) of formula (I)" refer to compound(s) of formula (I) as defined above including their salts, solvates and physiologically functional derivatives.

The amount of a compound of formula (I) which is required to achieve the desired biological effect will, of course, depend on a number of factors, for example, the specific compound chosen, the use for which it is intended, the mode of administration, and the clinical condition of the recipient. In general, a daily dose is expected to lie in the range of from 1 ng to 100 mg, typically from 50 ng to 50 mg, per day per kilogram bodyweight, for example 500 ng–5 mg/kg/day. An intravenous dose may, for example, be in the range of from 10 ng to 1 mg/kg which may conveniently be administered as an infusion of from 0.1 ng to 50 g per kilogram per minute. Infusion fluids suitable for this purpose may contain, for example, from 0.01 ng to 100 g, typically from 0.1 ng to 100 g, per milliliter. Unit doses, for example, may contain from 100 ng to 100 mg of the active compound; for example, ampoules for injection may contain from 100 ng to 1 mg and orally administrable unit dose formulations, such as tablets or capsules, may contain, for example, from 0.001 to 50 mg, typically from 0.02 to 20 mg. In the case of physiologically acceptable salts, the weights indicated above refer to the weight of the diaryl ion derived from the salt.

For the prophylaxis or treatment of the conditions referred to above, the compounds of formula (I) may be used as the compound per se, but are preferably presented with an acceptable carrier as a pharmaceutical formulation. The carrier must, of course, be acceptable in the sense of being compatible with the other ingredients of the formulation and not be deleterious to the recipient thereof. The carrier may be a solid or a liquid, or both, and is preferably formulated with the compound as a unit-dose formulation, for example, a tablet, which may contain from 0.05% to 95% by weight of active compound. Other pharmacologically active substances may also be present in formulations of the present invention. One or more of the compounds of formula (I) may be incorporated in the formulations of the invention, which may be prepared by any of the well known techniques of pharmacy consisting essentially of admixture of the components.

The formulations include those suitable for oral, rectal, topical buccal (e.g. sub-lingual), and parenteral (e.g. subcutaneous, intramuscular, intradermal, or intravenous) administration, although the most suitable route in any given case will depend on the nature and severity of the condition being treated and on the nature of the particular compound of formula (I), or the physiologically acceptable salt thereof, which is being used.

Formulations suitable for oral administration may be presented in discrete units, such as capsules, cachets, lozenges or tablets, each containing a predetermined amount of a compound of formula (I) or a physiologically acceptable salt thereof; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and the carrier (which may constitute one or more accessory ingredients). In general, the formulations are prepared by uniformly and intimately admixing the active compound with a liquid or finely divided solid carrier or both, and then, if necessary, shaping the product. For example, a tablet may be prepared by compressing or moulding a powder or granules of the compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Moulded tablets may be made by moulding, in a suitable machine, the powdered compound moistened with an inert liquid diluent.

Formulations suitable for buccal (sub-lingual) administration include lozenges comprising a compound of formula (I), or a physiologically acceptable salt thereof, in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of a compound of formula (I), or a physiologically acceptable salt thereof, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water and rendering the resulting solution sterile and isotonic with the blood. Injectable compositions according to the invention will generally contain from 0.1% to 5% w/w of active compound.

Formulations suitable for rectal administration are preferably presented as unit-dose suppositories. These may be prepared by admixing a compound of formula (I), or a physiologically acceptable salt thereof, with one or more conventional solid carriers, for example, cocoa butter, and then shaping the resulting mixture. Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w of the composition, for example, from 0.5 to 2%.

The compounds of formula (I) may be prepared in any conventional manner, for example, by the process described below. According to this aspect of the invention, compounds of formula (I) may be prepared by reacting a compound of formula (II)

W—P     (II)

wherein W is as hereinbefore defined and P is as defined below, with a compound of formula (III)

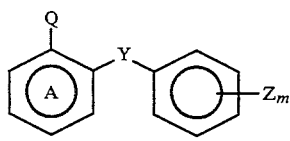     (III)

wherein m, Y and Z are as hereinbefore defined, ring A is optionally substituted as hereinbefore defined and Q is a nucleophilic group, for example, amino or hydroxy, capable of reacting with the group P, for example, isocyanate, in compound (II) or, alternatively, P in compound (II) is a nucleophilic group, for example, amino, capable of reacting with the group Q, for example, —CH$_2$CO$_2$H, in compound (III) to give a compound of formula (I). The reaction is typically carried out in a non-polar solvent, such as THF, in the presence of a suitable base, for example, DMAP.

Compounds of formula (III) may be prepared by reacting a compound of formula (IV)

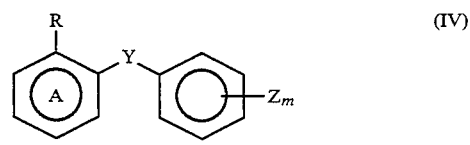     (IV)

wherein m, Y and Z are as hereinbefore defined, ring A is optionally substituted as hereinbefore defined, and R is a group capable of being converted to the group Q of compound (III), with a suitable reagent or reagents and under such conditions as to effect conversion of R to Q, for example, converting a nitro group to an amino group by catalytic hydrogenation.

Compounds of formula (IV) may be prepared by selectively reducing the carbonyl group of a compound of formula (V)

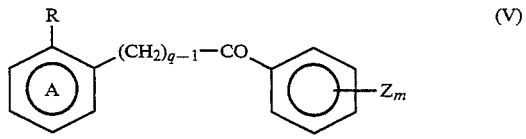     (V)

wherein m, q, R and Z are as hereinbefore defined and ring A is optionally substituted as hereinbefore defined, using, for example, triethylsilane in the presence of trifluoroacetic acid.

Compounds of formula (V) may be prepared by reacting a compound of formula (VI)

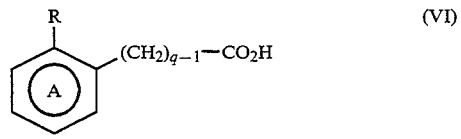     (VI)

wherein R and q are as hereinbefore defined and ring A is optionally substituted as hereinbefore defined, with a compound of formula (VII)

     (VII)

wherein m and Z is as hereinbefore defined, using, for example, Friedel-Crafts acylation conditions.

Compounds of formula (VI) may be prepared by reacting a compound of formula (VIII)

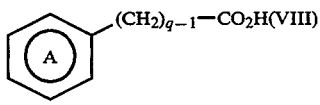

wherein q is as hereinbefore defined and ring A is optionally substituted as hereinbefore defined, with a suitable reagent or reagents and under such conditions as to substitute the group R of compound (VI) in the o-position, for example, in the case where R is nitro, by selective nitration using c.H$_2$SO$_4$/c.HNO$_3$ at low temperature.

Compounds of formulae (II) and (VII) are commercially available or may be prepared by methods well known to those skilled in the art or readily available from the chemical literature.

Optional conversion of a compound of formula (I) to a corresponding salt may be effected by reaction with the appropriate acid or base. Optional conversion to a physiologically functional derivative, such as an ester, may be carried out by methods well known to a skilled man or readily available from the chemical literature.

For a better understanding of the invention, the following Examples are given by way of illustration.

EXAMPLE 1

Preparation of N-heptyl-N'-(2,4-difluoro-6-{2-[4-(2,2-dimethylpropyl)phenyl]ethyl}phenyl)urea (a) 2-Nitro-3,5-difluorophenyl acetic acid A solution of 3,5-difluorophenylacetic acid (20 g, Fluorochem) in c.H$_2$SO$_4$ (150 ml) was stirred at −15° C. and c.HNO$_3$ (75 ml) added dropwise over 1 hour at a temperature of from −5° to −10° C. The mixture was stirred for a further ½ hour at −10° C. and then poured into ice-water (1.0 l). The latter was extracted with ether (×3) and the combined extracts washed with water (×2), dried over MgSO$_4$, and evaporated under reduced pressure to give a solid which was crystallised and then recrystallised from ether/hexane (1:4 v/v) to give 20.8 g of the desired product.

Analysis: Calcd C 44.24; H 2.30; N 6.45 Found C 44.18; H 2.38; N 6.24 200 MHz $^1$H NMR consistent with proposed structure.

(b) 2.4-Difluoro-6-[4-(2,2-dimethylpropyl)benzoylmethyl]-1-nitrobenzene

A suspension of the product from step (a) (10 g) in neopentyl benzene (40 ml, Fluka) was stirred at room temperature and oxalyl chloride (8.8 g) was added dropwise over 5 minutes, then DMF (5–10 drops). The mixture was stirred overnight at room temperature, then evaporated under reduced pressure to give an orange/yellow solution to which AlCl$_3$ (7.4 g) was added portionwise over 15 minutes. The resulting mixture was stirred for ½ hour at room temperature, followed by 4 hours at 60° C., then poured into ice/c.HCl (300 g/50 ml). The latter was extracted with ethyl acetate (×3) and the combined extracts washed with 2N HCl, 2N aqu. NaOH (×2), 2N HCl, and water (×2), dried over MgSO$_4$/charcoal, and evaporated under reduced pressure to give a brown oil which was flash chromatographed through a silica column using ether/hexane (3:7 v/v). The eluate was evaporated under reduced pressure and the residue crystallised from ether/hexane (1:3 v/v) to give 6.3 g of the desired product.

Analysis: Calcd C 65.72; H 5.5; N 3.99 Found C 65.71; H 5.48; N 4.03 200 MHz $^1$H NMR consistent with proposed structure.

(c) 2,4-Difluoro-6-{2-[4-(2,2-dimethylpropyl)phenyl]ethyl}-1-nitrobenzene

A solution of the product from step (b) (11.1 g) in trifluoroacetic acid (16 ml) was stirred at room temperature and triethylsilane (12.5 ml) added. The mixture was stirred overnight at room temperature, followed by 3 hours at 50° C. during which further portions of triethylsilane (3 ml each) were added after 1.5 hours and 2.5 hours, then poured into water (250 ml). The latter was extracted with ether (×2) and the combined extracts washed with water (×2), dried over MgSO$_4$, and evaporated under reduced pressure to give an oil which was flash chromatographed through a silica column using ether/hexane (1:4v/v). The eluate was evaporated under reduced pressure to give 11.0 g of the desired product.

Analysis: Calcd 68.47; H 6.31; N 4.20 Found 68.75; H 6.75; N 4.24 200 MHz $^1$H NMR consistent with proposed structure.

(d) 2,4-Difluoro-6-{2-[4-(2,2-dimethylpropyl)phenyl]ethyl}aniline

10% Pd/C (600 mg) was added under nitrogen to a stirred solution of the product from step (c) (10.9 g) in ethanol (150 ml) and the mixture hydrogenated at room temperature at a pressure of 1 atm. H$_2$ for 3.5 hours (uptake 2300 ml). The mixture was filtered, the residue washed with ethanol, and the filtrate evaporated under reduced pressure to give an oil which crystallised on standing to give 8.0 g of the desired product.

Analysis: Calcd C 75.25; H 7.59; N 4.62 Found C 75.61; H 8.01; N 4.62 200 MHz $^1$H NMR consistent with proposed structure.

(e) N-Heptyl-N'-(2,4-difluoro- 6-{2-[4-(2,2-dimethylpropyl)phenyl]-ethyl}phenyl)urea A solution of the product from step (d) (4.5 g) in THF (50 ml) was stirred at room temperature and heptyl isocyanate (5.5 g containing 36 mole % benzene, prepared by the method described in Organic Syntheses, Collective Volume 3, p.846) and N,N-dimethylaminopyridine (750 mg) were added. The mixture was stirred at room temperature for ca 60 hours, then evaporated under reduced pressure to give an oil which was flash chromatographed through a silica column using ether/hexane (2:1 v/v). The eluate was evaporated under reduced pressure and the residue crystallised from hexane and triturated with methanol to give 4.5 g of material. The latter was flash chromatographed through a silica column using ether/hexane (2:1 v/v) and then freeze-dried from dioxan to give 5.3 g of the desired product, mp 105°–107° C.

Analysis: Calcd C 72.97; H 8.56; N 6.31 Found C 72.16; H 8.45; N 6.17 200 MHz $^1$H NMR consistent with proposed structure.

SYNTHETIC EXAMPLES 2–30

The following compounds of formula (I) were prepared in a manner analogous to the method of Synthetic Example 1.

2) N-Heptyl-N'-{2-[2-(4-isobutylphenyl)ethyl]phenyl}urea, mp 105°–107° C.;

3) N-[2-{2-[4-(2,2-Dimethylpropyl)phenyl]ethyl}phenyl]-N'-heptylurea, colourless foam;

4) N-Heptyl-N'-{2-[3-(4-isobutylphenyl)propyl]phenyl}urea, mp 79°–82° C.;

5) N-Heptyl-N'-2-(4-isobutylphenylmethyl)phenylurea, mp 107°–109° C.;
6) N-Heptyl-N'-[2-(4-isobutylphenylvinyl)phenyl]urea, mp 86° C. (softens 78° C.);
7) N-{2-[2-(4-Isobutylphenyl)ethyl]phenyl-N-pencylurea, mp 105°–106° C.;
8) N-Decyl-N'-{2-[2-(4-isobutylphenyl)ethyl]phenyl}urea, mp 105°–107° C.;
9) N-Cyclohexanemethyl-N'-{2-[2-(4-isoburylphenyl)ethyl]phenyl}urea, mp 137°–139° C.;
10) N-{2-[2-(4-Isobutylphenyl)ethyl]phenyl}-2-bromodecanamide, mp 96°–97° C.;
11) N-{2-[2-(4-Isobutylphenyl)ethyl]phenyl}nonanethioamide, mp 34°–36° C.;
12) N-Heptyl-2-[2-(4-isobutylphenyl)ethyl]phenylacetamide, mp 50°–52° C.;
13) N-2-[2-(4-Isobutylphenyl)ethyl]phenyloxycarbonylheptylamine, mp 55°–57° C.;
14) N-Heptyl-N'-{2-[2-(4-isobutylphenyl)ethyl]-4,6-difluorophenyl}urea, mp 100°–102° C.;
15) N-Cyclohexyl-N'-{2-[2-(4-isobutylphenyl)ethyl]phenyl}urea, mp 143°–145° C.;
16) N-{2-[2-(4-Isobutylphenyl)ethyl]phenyl}-N'-nonylurea, mp 104°–107° C.;
17) N-{2-[2-(4-Isobutylphenyl)ethyl]phenyl}-N'-undecylurea, mp 98°–100° C.;
18) N-Benzyl-N'-{2-[2-(4-isobutylpbenyl)ethyl]phenyl}urea, mp 153°–154° C.;
19) N-{2-[2-(4-Isobutylphenyl)ethyl]phenyl}-N'-phenylurea, mp 161°–163° C.;
20) 2-[2-(4-Isobutylphenyl)ethyl]phenylurea, mp 171°–172° C.;
21) N-[(N-1-Butylcarbamoyl)methyl]-N'-{2-[2-(4-neopentylphenyl)ethyl-4,6-difluoro]phenyl}urea, mp 160°–161° C.;
22) N-[(N-1-Butylcarbamoyl)methyl]-N'-{2-[2-(4-neopentylphenyl)ethyl]phenyl)urea, mp 146°–147° C.;
23) N-(2-Butyramidoethyl)-N'-{2-[2-(4-neopentylphenyl)ethyl-4,6difluoro]phenyl}urea, no mp (lyophilisate);
24) N-{2-[2-(4-Isobutylphenyl)ethyl]benzyl-N'-hexylurea, mp 95° C.;
25) N-[2,4-Difluoro-6-(2-phenylethyl)phenyl]-N'-heptylurea, mp 111°–113° C.;
26) 2-Cyano-1-heptyl-3-{2-[2-(4-isobuuylphenyl)ethyl]phenyl}guanidine, mp 82°–84° C.;
27) {2,4-Difluoro-6-[4-(2,2-dimethylpropyl)benzyl]phenyl}-N-heptyl-carbamate, mp 58°–59° C.
28) {2,4-Difluoro-6-{2-[4-(2,2-dimethylpropyl)phenyl]-1-ethyl}-phenyl}-N-heptylcarbamate, mp 55°–56° C.;
29) N-(2-Ethyl-(2'-p-neopentylphenyl)-3,5-difluorophenyl)-2-bromodecanamide, mp 76°–78° C.
30) N-(1,1-Dimethylprop-2-ynyl)-N'-(2,4-difluoro-6-{2-[4-(2,2-dimethlpropyl)phenyl]ethyl}phenyl)urea, mp 145°–148° C.

The NMR's, IR's and elemental analyses of the compounds of Examples 2 to 30 were all consistent with the proposed structures.

Pharmaceutical Formulation Examples

In the following Examples, the "active ingredient" is any compound of formula (I) as hereinbefore defined, preferably one of the compounds of Synthetic Examples 1 to 30, most preferably the compound of Synthetic Example 1.

(i) Tablet formulations

The following formulations A., B and C may be prepared by wet granulation of ingredients (a) to (c), (a) to (d) and (a) to (c) respectively with a solution of povidone, followed by addition of the magnesium stearate and compression.

|  | mg/tablet | mg/tablet |
|---|---|---|
| Formulation A |  |  |
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
|  | 500 | 300 |
| Formulation B |  |  |
| (a) Active ingredient | 250 | 250 |
| (b) Lactose 150 | 150 | — |
| (c) Avicel PH 101 | 60 | 26 |
| (d) Sodium Starch Glycollate | 20 | 12 |
| (e) Povidone B.P. | 15 | 9 |
| (f) Magnesium Stearate | 5 | 3 |
|  | 500 | 300 |
| Formulation C |  |  |
| (a) Active ingredient | 100 |  |
| (b) Lactose | 200 |  |
| (c) Starch | 50 |  |
| (d) Povidone | 5 |  |
| (e) Magnesium Stearate | 4 |  |
|  | 359 |  |

The following formulations D and E may be prepared by direct compression of the admixed ingredients. The lactose used in formulation E is of the direct compression type.

| Formulation D | mg/capsule |
|---|---|
| Active ingredient | 250 |
| Magnesium Stearate | 4 |
| Pregelatinised Starch NF15 | 146 |
|  | 400 |
| Formulation E | mg/capsule |
| Active ingredient | 250 |
| Magnesium Stearate | 5 |
| Lactose | 145 |
| Avicel | 100 |
|  | 500 |
| Formulation F (Controlled release formulation) | mg/tablet |
| (a) Active ingredient | 500 |
| (b) Hydroxypropylmethylcellulos (Methocel K4M Premium) | 112 |
| (c) Lactose B.P. | 53 |
| (d) Povidone B.P.C. | 28 |
| (e) Magnesium Stearate | 7 |
|  | 700 |

The formulation may be prepared by wet granulation of ingredients (a) to (c) with a solution of povidone, followed by addition of the magnesium stearate and compression.

(ii) Capsule formulations

Formulation A

Capsules may be prepared by admixing the ingredients of Formulation D above and filling two-part hard gelatin capsules with the resulting mixture. Formulation B (infra) may be prepared in a similar manner.

|  | mg/capsule |
|---|---|
| Formulation B |  |

|  | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
| | 420 |
| Formulation C | |
| (a) Active ingredient | 250 |
| (b) Macrogel 4000 BP | 350 |
| | 600 |

Capsules may be prepared by melting the Macrogel 4000 BP, dispersing the active ingredient in the melt, and filling two-part hard gelatin capsules therewith.

| Formulation D | mg/capsule |
|---|---|
| Active ingredient | 250 |
| Lecithin | 100 |
| Arachis Oil | 100 |
| | 450 |

Capsules may be prepared by dispersing the active ingredient in the lecithin and arachis oil and filling soft, elastic gelatin capsules with the dispersion.

| Formulation E (Controlled release capsule) | mg/capsule |
|---|---|
| (a) Active ingredient | 250 |
| (b) Microcrystalline Cellulose | 125 |
| (c) Lactose BP | 125 |
| (d) Ethyl Cellulose | 13 |
| | 513 |

The controlled-release capsule formulation may be prepared by extruding mixed ingredients (a) to (c) using an extruder, then spheronising and drying the extrudate. The dried pellets are coated with ethyl cellulose (d) as a controlled-release membrane and filled into two-part hard gelatin capsules.

(iii) Intravenous injection formulation
Active ingredient 0.200 g
Sterile, pyrogen-free phosphate buffer (pH 9.0) to 10 ml The active ingredient is dissolved in most of the phosphate buffer at 35°-40° C., then made up to volume and filtered through a sterile micropore filter into sterile 10 ml glass vials (Type 1) which are sealed with sterile closures and overseals.

| (iv) Intramuscular injection formulation | |
|---|---|
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| (v) Syrup formulation | |
|---|---|
| Active ingredient | 0.2500 g |
| Sorbitol Solution | 1.5000 g |
| Glycerol | 1.0000 g |
| Sodium Benzoate | 0.0050 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| (vi) Suppository formulation | mg/suppository |
|---|---|
| Active ingredient (63 μm)* | 250 |
| Hard Fat, BP (Witepsol H15 - Dynamit Nobel) | 1770 |
| | 2020 |

\* The active ingredient is used as a powder wherein at least 90% of particles are of 63 μm diameter or less.

One-fifth of the Witepsol H15 is melted in a steam-jacketed pan at 45° C. maximum. The active ingredient is sifted through a 200 μm sieve and added to the molten Base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 μm stainless steel screen and, with continuous stirring, allowed to cool to 40° C. At a temperature of 38°-40° C., 2.02 g aliquots of the mixture are filled into suitable plastic moulds and the suppositories allowed to cool to room temperature.

| (vii) Pessary formulation | mg/pessary |
|---|---|
| Active ingredient (63 μm) | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

Biological assay
In vitro inhibition of ACAT
The in vitro esterification of cholesterol in the presence of ACAT and the test compound was assayed radiometrically using [$^{14}$C]oleoyl CoA as substrate:

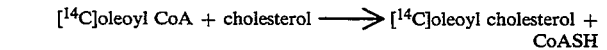

[$^{14}$C]oleoyl CoA + cholesterol ⟶ [$^{14}$C]oleoyl cholesterol + CoASH

The enzyme is membrane-associated in vivo. Microsomal protein is therefore used as the source of both ACAT and cholesterol. The compounds of the invention were tested against enzyme derived from human embryo 407 intestinal epithelial cell line.

[$^{14}$C]Oleoyl CoA was incubated with microsomal protein at 37° C., pH 7.0, in the presence of various concentrations of the test compound. After 4 minutes, the reaction was stopped by the addition of ice-cold chloroform/methanol containing a known amount of [$^{3}$H]oleoyl cholesterol to compensate for the loss of any [$^{14}$C]product. A known volume of the resulting lower phase, which contains lipidic material from the reaction, was dried, redissolved in hexane containing unlabelled oleoyl cholesterol (TLC marker), and run on a quantitative TLC plate (silica gel). The oleoyl cholesterol spot was visualised (iodine vapour), removed from the TLC plate, and its radioactivity measured by scintillation counting.

A plot of ACAT inhibitory activity vs concentration was prepared for each test compound and the corresponding $IC_{50}$ determined. The compounds of Synthetic Examples 1 to 30 were all found to significantly inhibit ACAT. The compound of Synthetic Example 1, for example, gave an $IC_{50}$ for ACAT inhibition of 0.022 μM.

Toxicity

The cytotoxicity of the compound of Synthetic Example 1 was investigated in vitro by studying its effects on the metabolic competence of isolated rat liver cells. No effect on gluconeogenesis was observed at concentrations of up to 100 μM. A 15% decrease in ATP levels was observed after 90 minutes at a concentration of 100 μM.

We claim:

1. A method for the prophylaxis or treatment of atherosclerosis in a mammal which comprises the administration to a mammal of a therapeutically effective amount of the compound N-heptyl-N'-(2,4-difluoro-6-{2-[4-(2,2-dimethylpropyl)phenyl]ethyl}phenylurea or a physiologically acceptable salt or solvate thereof.

2. The method of claim 1 in which the mammal is a human.

* * * * *